(12) United States Patent
Roe

(10) Patent No.: US 8,399,515 B2
(45) Date of Patent: Mar. 19, 2013

(54) FIVE AND FIFTEEN CARBON FATTY ACIDS FOR TREATING METABOLIC DISORDERS AND AS NUTRITIONAL SUPPLEMENTS

(75) Inventor: Charles R. Roe, Rockwall, TX (US)

(73) Assignee: Baylor Research Institute, Dallas, TX (US)

( * ) Notice: Subject to any disclaimer, the term of this patent is extended or adjusted under 35 U.S.C. 154(b) by 0 days.

(21) Appl. No.: 10/557,310

(22) PCT Filed: May 19, 2004

(86) PCT No.: PCT/US2004/015633
§ 371 (c)(1),
(2), (4) Date: Oct. 30, 2006

(87) PCT Pub. No.: WO2004/103307
PCT Pub. Date: Dec. 2, 2004

(65) Prior Publication Data
US 2007/0123588 A1    May 31, 2007

Related U.S. Application Data

(60) Provisional application No. 60/471,949, filed on May 20, 2003.

(51) Int. Cl.
*A61K 31/20* (2006.01)
*A61K 31/14* (2006.01)

(52) U.S. Cl. .................................. 514/558; 514/642
(58) Field of Classification Search .................. 514/558, 514/642
See application file for complete search history.

(56) References Cited

U.S. PATENT DOCUMENTS 5,153,221 A    10/1992    Revici
6,740,679 B1   5/2004     Roe

OTHER PUBLICATIONS

European Supplementary Search Report for EP 04752622.3 dated Nov. 14, 2008.
Liakopoulou, et al., "Stimulation of Fetal Hemoglobin Production by Short Chain Fatty Acids," Blood (1995), 86:3227-3235.
Odle, et al., "Improving Piglet Survival by Nutritional Means: Efforts to Enhance the Efficacy of Medium-Chain Triglycerides," Journal of Animal Science (1992), 70:61 (Abstract).
Roe, et al., "Treatment of cardiomyopathy and rabdfomyolysis in long-chain fat oxidation disorders using anaplerotic odd-chain triglyceride," Journal of Clinical Investigation (2002), 110:259-269.
Van Kempen, et al., "Quantification of carnitine esters by high-performance liquid chromatography: Effect of feeding medium-chain triglycerides on the plasma carnitine esters profile," Journal of Chromatography Biomedical Applications (1992), 584:157-165.
International Search Report for PCT/US2004/15633, dated Jan. 6, 2005, 2 pages.

*Primary Examiner* — Zohreh Fay
(74) *Attorney, Agent, or Firm* — Cooley LLP

(57) ABSTRACT

According to the present invention, acquired metabolic derangements or fatty acid disorders in humans that are manifested by a deficiency in at least one enzyme involved in fatty acid metabolism are treated with a five carbon or a fifteen carbon fatty acid source. Rapid nutritional supplementation can also be provided to a mammalian cell by providing either a five carbon or fifteen carbon fatty acid source. Dietary formulations suitable for human consumption comprising either a five carbon fatty acid, a fifteen carbon fatty acid or triglycerides thereof is also disclosed.

12 Claims, 4 Drawing Sheets

FIVE AND FIFTEEN CARBON FATTY ACIDS FOR TREATING METABOLIC DISORDERS AND AS NUTRITIONAL SUPPLEMENTS

CROSS-REFERENCE TO RELATED APPLICATION

This application is a National Stage entry under 35 U.S.C. §371 of International Patent Application No. PCT/US04/15633 filed May 19, 2004 which claims the benefit of U.S. Provisional Patent Application No. 60/471,949 filed May 20, 2003.

TECHNICAL FIELD OF THE INVENTION

The invention relates to methods of treating inherited metabolic disorders and acquired metabolic derangements and nutritional supplements for normal humans and animals.

BACKGROUND OF THE INVENTION

Fatty acid oxidation disorders (FODs) can cause serious clinical manifestations or even death. There have been a variety of inherited metabolic FODs identified which are enzyme deficiencies, and there are also various acquired metabolic derangements manifested by inadequate energy reaching particular muscles, such as the heart under stress conditions. In addition, normal individuals experience nutritional inefficiencies due to metabolism of the food choices that they make.

Previously, the use of a seven carbon fatty acid was found to be effective in a method for treating an inherited disorder in at least one enzyme involved in fatty acid metabolism. This use was described and claimed in U.S. Ser. No. 09/890,559, filed Aug. 1, 2001 which is hereby incorporated by reference. U.S. Ser. No. 09/890,559 claims priority to U.S. Provisional Application 60/119,038 filed 5 Feb. 1999 and PCT/US00/03022 filed 3 Feb. 2000. In that work, seven carbon fatty acids were also found to be effective as an energy source for humans not suffering from an enzyme deficiency, but in need of nutrients that provide fuel for a metabolic pathway that is underutilized due to the lack of odd chain fatty acids in normal foodstuffs.

For individuals suffering from Medium Chain Acyl-CoA Dehydrogenase (MCAD) Deficiency, an inherited metabolic disorder characterized by a deficiency of the enzyme medium chain acyl-CoA dehydrogenase, there remained a need for a treatment other than the administration of seven carbon fatty acids. MCAD participates in the initial oxidation of seven carbon fatty acids; therefore deficiency of MCAD cannot be treated with seven carbon fatty acids. Conventional dietary therapy for MCAD patients is to eat a high carbohydrate, fat restricted diet, avoiding fasting and eating often throughout the day. However, there is no reliable parenteral approach for rescue of MCAD patients during crisis. Further, dietary control is more difficult with infants since some of the enzymes needed by humans to metabolize certain carbohydrates, such as starches, do not become active until nearly six months of age. Cornstarches may be useful for treatment of babies and children above six months of age, but may cause undesirable effects such as constipation.

It has now been found that five carbon fatty acids are useful as a treatment for MCAD. Further, five carbon fatty acids can be used to treat long-chain FODs that are also treatable with seven carbon fatty acids. Five carbon fatty acids present a metabolic profile differing from that presented upon administration of seven carbon fatty acids, and this may be advantageous in some circumstances.

Further, it has been found that a fifteen carbon fatty acid (C15) can be administered as a precursor to five carbon fatty acids in normal humans and animals and for certain metabolic disease states such as Short-chain acyl-CoA dehydrogenase (SCAD) deficiency, and are preferred to C5 fatty acids for oral administration. C5 fatty acids have been found to have an undesirable taste due to breakdown by enzymes present in the saliva, and such enzymes are not active on C15 compounds and therefore C15 has a more pleasant taste.

SUMMARY OF THE INVENTION

In one aspect, the invention is a method for treating acquired metabolic derangements or fatty acid disorders in humans that are manifested by a deficiency in at least one enzyme involved in fatty acid metabolism, comprising treating the human with a five carbon fatty acid source. The treatment can be used for treating fatty acid disorders including but not limited to MCAD, SCAD, VLCAD, MTP, and LCHAD fatty acid disorders. The treatment is useful for acquired metabolic derangement concerning increased metabolic needs by cardiac tissue.

In another aspect, the invention is a method for treating fatty acid disorders in humans that are manifested by a deficiency in at least one enzyme involved in fatty acid metabolism, comprising treating the human with a fifteen carbon fatty acid source. The treatment can be used to treat fatty acid disorders including but not limited to SCAD. In one exemplary method, the fifteen carbon fatty acid is administered orally.

In another aspect, the invention is a method for providing rapid nutritional supplementation to a mammalian cell, comprising providing a five carbon fatty acid source to the cell.

In another aspect, the invention is a method for providing rapid nutritional supplementation to a mammalian cell, comprising providing a fifteen carbon fatty acid source to the cell. In one exemplary method, administration is oral.

In another aspect, the invention is a method for providing nutritional supplementation to a human or animal, comprising providing a fatty acid source comprising five carbons, administered enterally or parenterally.

In another aspect, the invention is a method for providing nutritional supplementation to a human or animal, comprising providing a fatty acid source comprising fifteen carbons, administered enterally or parenterally.

In another aspect, the invention is a dietary formulation suitable for human consumption comprising an odd numbered carbon chain fatty acid selected from the group consisting of five carbon fatty acids and fifteen carbon fatty acids and triglycerides thereof. In a preferred dietary formulation, the fatty acid is pentanoic acid. In one embodiment, the formulation is adapted for consumption by a human during a 24 hour time period and comprises from about 15 to about 40% of the dietary caloric requirement of the human for the 24 hour time period. In another embodiment, the formulation is adapted for consumption by a human during a 24 hour time period and comprises from about 20 to about 35% of the dietary caloric requirement of the human for the 24 hour time period. In yet another embodiment, the formulation is adapted for consumption by a human during a 24 hour time period and comprises about 25-35% of the dietary caloric requirement of the human for the 24 hour time period. According to the present invention, these formulations are generally suitable for enteral administration and parenteral administration, and with the exception of pentanoic acid, oral consumption.

DETAILED DESCRIPTION OF THE INVENTION

It has now been found that odd-carbon fatty acids comprising five carbon fatty acids (C5) or fifteen carbon fatty acids (C15) can be used to treat inherited metabolic disorders in humans and acquired metabolic derangements (e.g., congestive heart failure, cardiomyopathy) in humans and other mammals. These fatty acid sources may also be used for enhanced nutrition of normal, non-diseased humans and animals.

Figure 1:
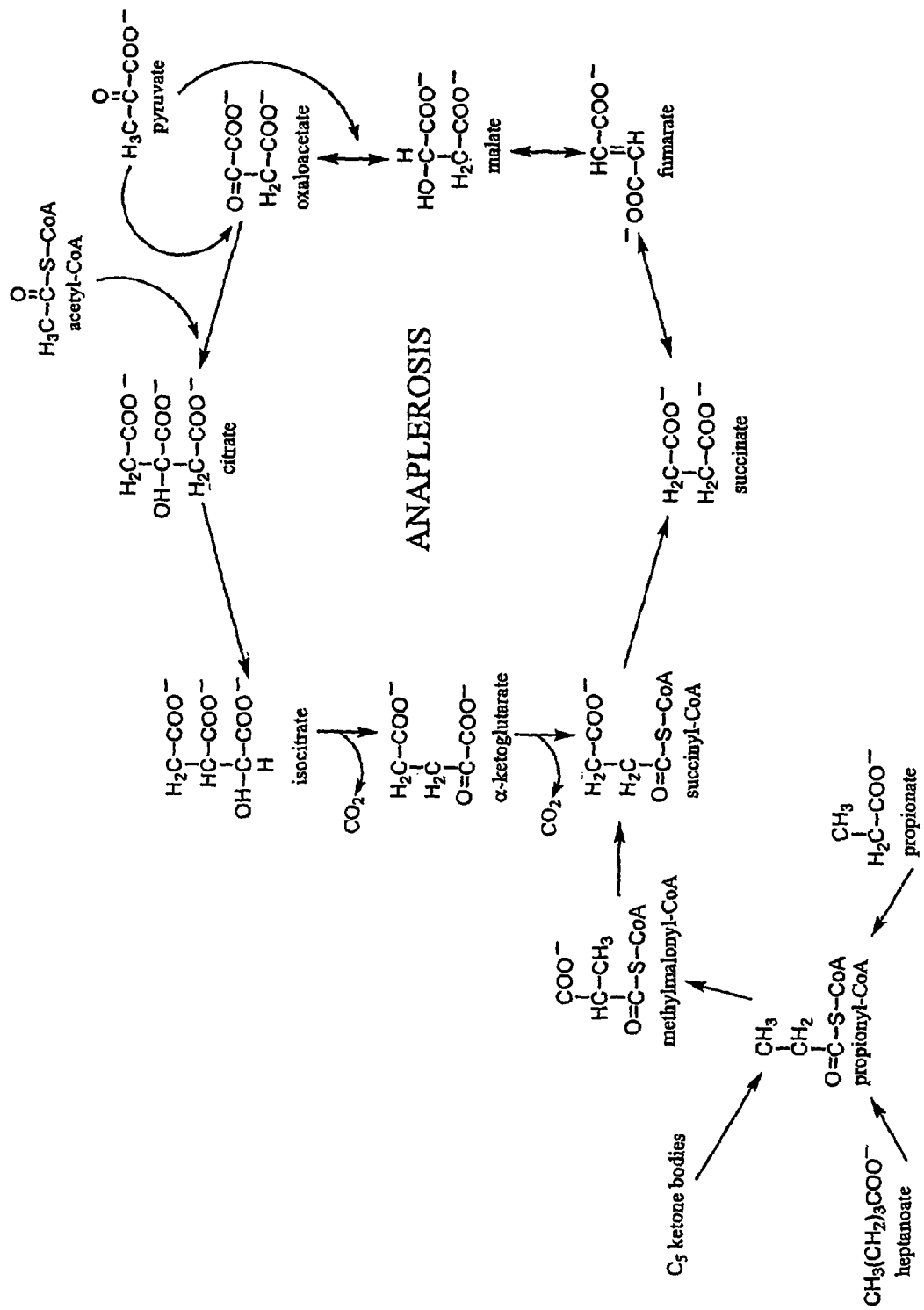
FIG. 1 depicts the use of propionyl-CoA and acetyl-CoA in the Citric Acid Cycle.
Figure 2:
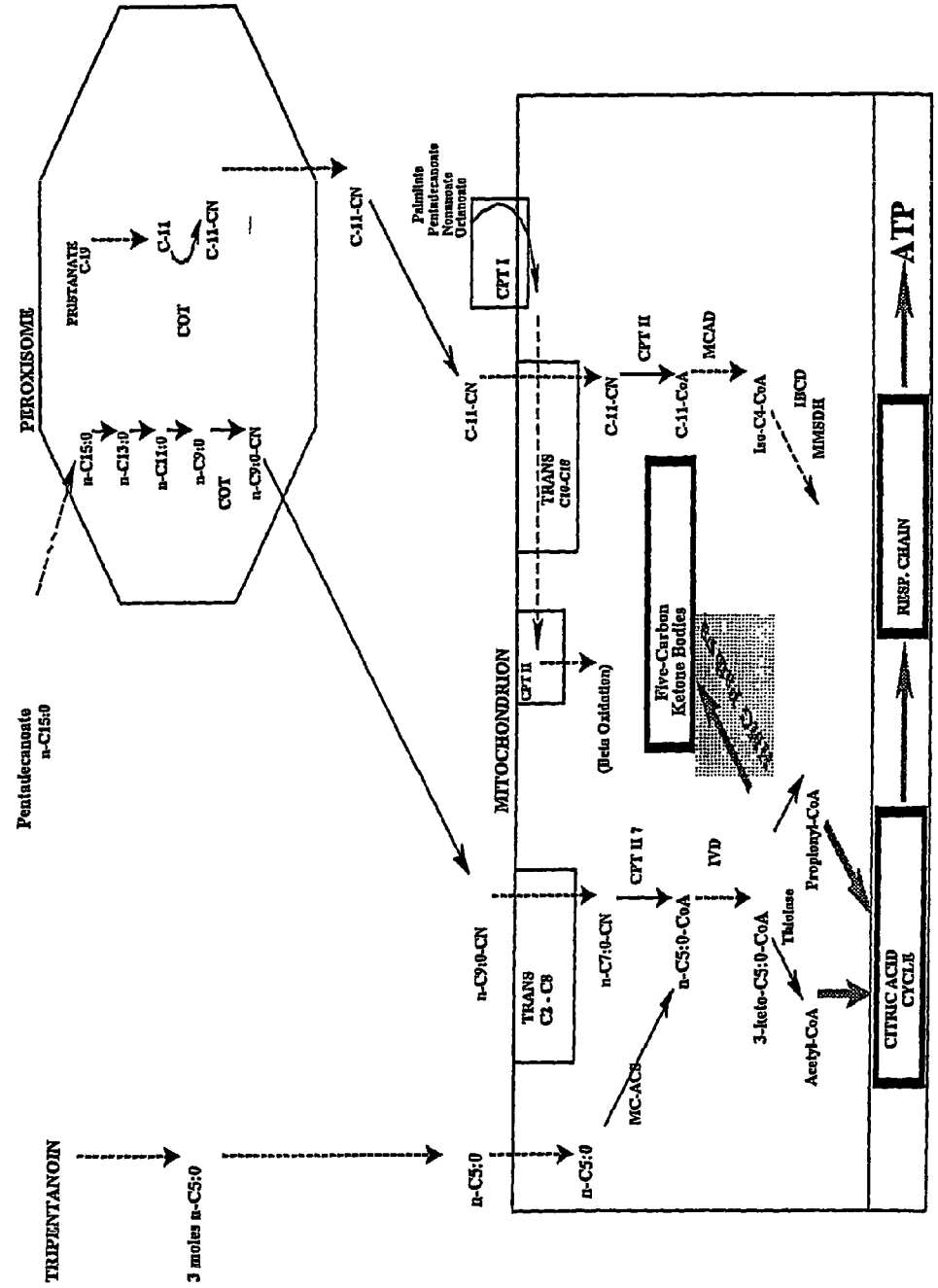
FIG. 2 depicts the oxidation of tripentanoin in the mitochondrion and pentadecanoate in the peroxisome and mitochondrion.

Metabolism of these source fatty acid sources is effective to provide, simultaneously, propionyl-CoA and acetyl-CoA inside the mitochondrion. Provision of these two CoA thioesters is useful for four main reasons: (1) they participate in anaplerosis, or the filling up with intermediates, of the Citric Acid Cycle (CAC), thereby enhancing the rotation of the CAC, which results in enhanced production of ATP via proton transfer from reduced co-enzymes (FADH and NADH) to the respiratory chain; (2) acetyl-CoA participates in the citrate synthase reaction which produces citrate in the CAC; (3) both acetyl-CoA and propionyl-CoA stimulate the production of oxaloacetate, which is gluconeogenic; and (4) the metabolism of odd-chain fatty acid C15 via mitochondrial beta oxidation is also ketogenic, since the metabolism of the ketones formed results in additional acetyl-CoA and propionyl-CoA in the mitochondria. A representation of the entry of acetyl-CoA, propionyl-CoA into the CAC is provided in FIG. 1 and a representation of oxidation of tripentanoin (C5) and pentadecanoate (C15) is provided in FIG. 2.

In one embodiment of the invention, a C5 or a C15 fatty acid source is provided for enteral administration or consumption by a person in need of treatment or nutritional supplementation. Tripentanoin can be obtained by the esterification of n-pentanoic acid, which is commercially available (Sigma Chemical Company, St. Louis Mo.), and glycerol by methodology known in the art for the making of triglycerides. As used herein, a C5 fatty acid source may be the fatty acid or its triglyceride. A C15 fatty acid source, n-pentadecanoic acid (C15) is also commercially available. (Sigma). A C-15 triglyceride may be made by esterification with glycerol through methods known in the art. Preferred types of enteral administration are oral, parenteral and nasogastric administration. Although it is subject to all types of enteral administration, it is most preferred that when a C5 fatty acid is used, that it be administered non-orally, since it has a disagreeable taste. It has been found that C15 does not have a disagreeable taste, and that oral administration of C15 is more preferred over oral administration of C5. C15 is most preferred over C5 in foods and beverages used for nutritional supplementation, since it has an agreeable taste and since it serves as a metabolic precursor for C5 and therefore for propionyl-CoA and acetyl-CoA.

The amount of C5 or C15 fatty acid to provide to a human in need of treatment for an inherited metabolic disorder or acquired metabolic derangement is from 15 to 40% of the daily dietary caloric requirement. Preferably, the amount supplied will be from about 25-35% and most preferred about 35%. If C5 or C15 is used as a nutritional supplement, it is advantageous in any amount as an additive to food, beverages, or parenteral nutrient formulas. However, it is most advantageous to provide the fatty acids in the same amounts useful for treatment.

The efficacy of pentadecanoate [C15] and pentanoate [C5] for treating fat oxidation disorders is demonstrated in Table 1. Data is compared with that obtained for treatment with heptanoate [C7], an odd carbon fatty acid earlier found useful for treatment of certain disorders. (See PCT WO 00/45649, published Oct. 8, 2000).

Fibroblasts obtained from patients with inherited defects of mitochondrial fat oxidation were cultured in the presence of omega deuterated odd-carbon numbered fatty acids, as described in Roe, C. R., Sweetman, L., Roe, D. S., David, F., Brunengraber, H., "Effective Dietary Treatment of Cardiomyopathy & Rhabdomyolysis in Long-Chain Fat Oxidation Disorders using an Anaplerotic Odd-Chain Triglyceride," *J. Clin. Invest.* 110 (2): 259-269 (2002).

The relative amounts of the precursors as acylcarnitines and the relative amounts of propionyl-CoA (as propionylcarnitine [C3] produced after 72 hours incubation provides information as to whether the tested fatty acid is useful for producing propionyl-CoA in the various defective fibroblast cell lines. These results reflect the presence of the required enzyme systems for dietary therapy.

The data in Table 1 represents testing of cultured fibroblasts derived from ten patients afflicted with Very-long-chain acyl-CoA dehydrogenase (VLCAD) deficiency (six patients with the severe cardiac form and four with the non-cardiac milder phenotype), two patients with Mitochondrial Trifunctional Protein (MTP) deficiency, five patients having L-3-hydroxy-acyl-CoA dehydrogenase (LCHAD) deficiency and three patients with Short-chain acyl-CoA dehydrogenase (SCAD) deficiency.

Results of incubations with C5 fatty acid for all of these cell lines produced consistently greater quantities of propionylcarnitine than was observed with the same cells incubated with heptanoate (C7). This is reflected in the ratios of the amount of propionylcarnitine produced by C5 compared to the amount from C7.

TABLE 1

Propionylcarnitine from Oxidation of Odd-Carbon Fatty Acids in Fibroblasts (Results in nmol/mg Protein/72 hours)

| Disease | No. Carbons in Fatty Acid | | | Ratio: C5/C7 | Ratio: C5/C15 |
|---|---|---|---|---|---|
| | C5 | C7 | C15 | | |
| VLCAD | 28.2 | 17.8 | 8.0 | 1.6 | 3.5 |
| Cardiac | 34.7 | 20.4 | 6.6 | 1.7 | 5.3 |
| | 50.6 | 25.0 | 9.9 | 2.0 | 5.1 |
| | 47.0 | 28.7 | 11.7 | 1.6 | 4.0 |
| | 27.2 | 13.0 | 5.3 | 2.1 | 5.2 |
| | 67.8 | 44.5 | 21.6 | 1.5 | 3.1 |
| | | | | AVG. 1.8 | AVG. 4.4 |

TABLE 1-continued

Propionylcarnitine from Oxidation of Odd-Carbon Fatty Acids in Fibroblasts (Results in nmol/mg Protein/72 hours)

| Disease | No. Carbons in Fatty Acid | | | Ratio: C5/C7 | Ratio: C5/C15 |
|---|---|---|---|---|---|
| | C5 | C7 | C15 | | |
| VLCAD | 44.4 | 22.6 | 16.4 | 2.0 | 2.7 |
| Non-Cardiac | 28.3 | 20.3 | 19.2 | 1.4 | 1.5 |
| | 51.8 | 24.3 | 36.0 | 2.1 | 1.4 |
| | 19.7 | 14.4 | 11.5 | 1.4 | 1.7 |
| | | | | AVG. 1.7 | AVG. 1.8 |
| MTP | 38.3 | 24.1 | 31.4 | 1.6 | 1.2 |
| | 63.6 | 48.1 | 46.5 | 1.3 | 1.4 |
| | | | | AVG. 1.5 | AVG. 1.3 |
| LCHAD | 65.4 | 53.2 | 34.6 | 1.2 | 1.9 |
| | 34.5 | 23.5 | 15.1 | 1.5 | 2.3 |
| | 35.0 | 24.0 | 15.9 | 1.5 | 2.2 |
| | 24.4 | 10.6 | 6.9 | 2.3 | 3.5 |
| | 36.8 | 22.7 | 13.9 | 1.6 | 2.6 |
| | | | | AVG. 1.6 | AVG. 2.5 |
| SCAD | 80.2 | 57.7 | 56.7 | 1.4 | 1.4 |
| | 43.6 | 32.4 | 30.3 | 1.4 | 1.4 |
| | 48.2 | 39.2 | 37.6 | 1.2 | 1.3 |
| | | | | AVG. 1.3 | AVG. 1.4 |

VLCAD—Very-Long-Chain Acyl-CoA Dehydrogenase Deficiency (Cardiac and Non-Cardiac)
MTP—Mitochondrial Trifunctional Protein Deficiency
LCHAD—L-3-Hydroxy-Acyl-CoA Dehydrogenase Deficiency
SCAD—Short-Chain Acyl-CoA Dehydrogenase Deficiency It has been found, however, that although there is no bad taste associated with oral administration of triheptanoin (C7), there is a very bad taste when tripentanoin (C5) is used as a fatty acid source, due to cleavage of the triglyceride by salivary enzymes that yields free valeric acid and mono- and diglycerides. However, for nasogastric, gastrostomy, or parenteral feeding, tripentanoin (C5) is advantageous for treatment of all fat oxidation disorders, including MCAD deficiency, as well as other diseases of amino acid metabolism that do not involve enzymes of the HMG pathway (ketogenesis) or ketone utilization.

Although application of equivalent amounts of C15 fatty acids yielded less propionylcarnitine than did application of C5 or C7 fatty acids, C15 fatty acids were also found effective in providing propionyl-CoA to the Kreb's cycle. Particularly in the case of normals and humans with SCAD deficiency, the amount of propionyl-CoA produced upon provision of C15 approaches that produced upon provision of a C7 source. In contrast, C7 was found to be more efficient than C15 for VLCAD, MTP, and LCHAD cells.

It has also been found that C5-fatty acid sources are useful in a method for treating MCAD (Medium chain acyl-CoA dehydrogenase) deficiency. It has been found that odd-carbon fatty acids containing seven or more carbons require medium chain acyl-CoA dehydrogenase for oxidation. (Table 2). It is demonstrated in Table 3 that C5 fatty acids are effective in providing energy to cells even when medium chain acyl-CoA dehydrogenase is missing.

Fibroblasts from four patients with MCAD deficiency and one heterozygote (carrier) indicate that odd-carbon fatty acids containing more than seven carbons can not be effectively used in that disease. Incubation of MCAD deficient fibroblasts with C15 illustrates a block in oxidation at C9 & C7 (substrate chain-length requiring the MCAD enzyme). Incubation with C9 is associated with accumulation of C9 as expected for the same reason. Similarly, C7 is blocked, indicating that the MCAD enzyme is required for its oxidation. The C3 produced from these odd-carbon compounds is significantly reduced as expected. That any C3 was produced is presumably due to overlapping

TABLE 2

Fate of Odd-Carbon Fatty Acids in MCAD-Deficient Fibroblasts

TRIPENTADECANOIN (C15 triglyceride)

| MCAD | *C3 | *C5 | *C7 | *C9 | *C11 | *C13 | *C15 |
|---|---|---|---|---|---|---|---|
| Mean | 9.8 | 1.2 | 6.5 | 10.9 | 0.7 | 0.4 | 2.6 |
| SD | 7.0 | 0.5 | 3.1 | 5.7 | 0.3 | 0.4 | 1.6 |
| SEM | 3.5 | 0.2 | 1.5 | 2.8 | 0.2 | 0.2 | 0.8 |
| Minimum | 3.1 | 0.5 | 3.5 | 4.3 | 0.3 | 0.0 | 1.0 |
| Maximum | 19.6 | 1.6 | 9.9 | 17.5 | 1.0 | 0.9 | 4.7 |
| N | 4 | 4 | 4 | 4 | 4 | 4 | 4 |
| MCAD Carrier | 33.5 | 1.7 | 0.6 | 1.7 | 0.5 | 0.2 | 1.9 |
| CONTROL MEAN | 46.8 | 2.8 | 0.8 | 2.2 | 0.9 | 0.7 | 3.8 |
| S.D. (N = 4) | 8.8 | 0.7 | 0.5 | 2.0 | 0.6 | 0.6 | 1.77 |

TRINONANOIN (C9 triglyceride)

| MCAD | *C3 | *C5 | *C7 | *C9 |
|---|---|---|---|---|
| Mean | 3.0 | 0.5 | 2.8 | 7.3 |
| SD | 1.8 | 0.1 | 1.1 | 2.6 |
| SEM | 0.9 | 0.1 | 0.5 | 1.3 |
| Minimum | 1.6 | 0.3 | 1.6 | 4.0 |
| Maximum | 5.5 | 0.7 | 4.2 | 10.3 |
| N | 4 | 4 | 4 | 4 |
| MCAD Carrier | 6.0 | 0.4 | 0.4 | 3.2 |
| CONTROL MEAN | 3.9 | 0.4 | 0.3 | 2.0 |
| S.D. (N = 4) | 1.5 | 0.2 | 0.1 | 0.6 |

TRIHEPTANOIN (C7 triglyceride)

| MCAD | *C3 | *C5 | *C7 |
|---|---|---|---|
| Mean | 8.3 | 1.1 | 8.3 |
| SD | 4.8 | 0.5 | 4.2 |
| SEM | 2.4 | 0.2 | 2.1 |
| Minimum | 5.7 | 0.7 | 2.4 |
| Maximum | 15.4 | 1.8 | 12.0 |
| N | 4 | 4 | 4 |
| MCAD Carrier | 16.3 | 0.9 | 0.5 |
| CONTROL MEAN | 24.3 | 1.3 | 0.4 |
| S.D. (N = 4) | 5.6 | 0.3 | 0.2 |

TABLE 3

Propionylcarnitine from Odd Carbon Precursors-MCAD Fibroblasts (nmol/mg Protein/72 hours)

| PRECURSOR | NORMAL | MCAD-1 | MCAD-2 |
|---|---|---|---|
| C15 | 46.8 | 6.9 | 19.6 |
| C9 | 3.9 | 1.8 | 2.9 |
| C7 | 24.3 | 10.6 | 17.4 |
| C5 | 25.8 | 25.8 | 58.5 | chain-length specificity of other short chain acyl-CoA dehydrogenases in the mitochondrial matrix.

Experiments with 2 MCAD deficient fibroblast cell lines (MCAD 1 and MCAD 2) revealed that C5 was very effective for producing propionyl-CoA, in vitro, compared to pentadecanoate (C15), nonanoate (C9), or heptanoate (C7). Using a C5 fatty acid source produced normal or greater than normal propionyl-CoA in culture. It was also found that C15 is more effective in normal cells in boosting the production of propionyl-CoA than C7 or C5 (which are comparable). Therefore, C15 is a candidate for use in nutritional supplementation of normal patients.

EXAMPLE 1

Use of Tripentanoin to Treat Patients with Fat Oxidation Disorders (VLCAD and SCAD)

A VLCAD patient and an SCAD patient, both of whom had gastrostomy sites for enteral administration, each were provided with separate meals containing equimolar amounts of triheptanoin (C7) and tripentanoin (C5) at different times on the same day. Each patient was given the amount in 1 of 4 daily meals equivalent to a diet of 3 gms/Kg/day or about 30% of total Kcal as the triglyceride. Serial blood samples were obtained hourly and individual urines were collected at baseline and during the meal.

Figure 3:
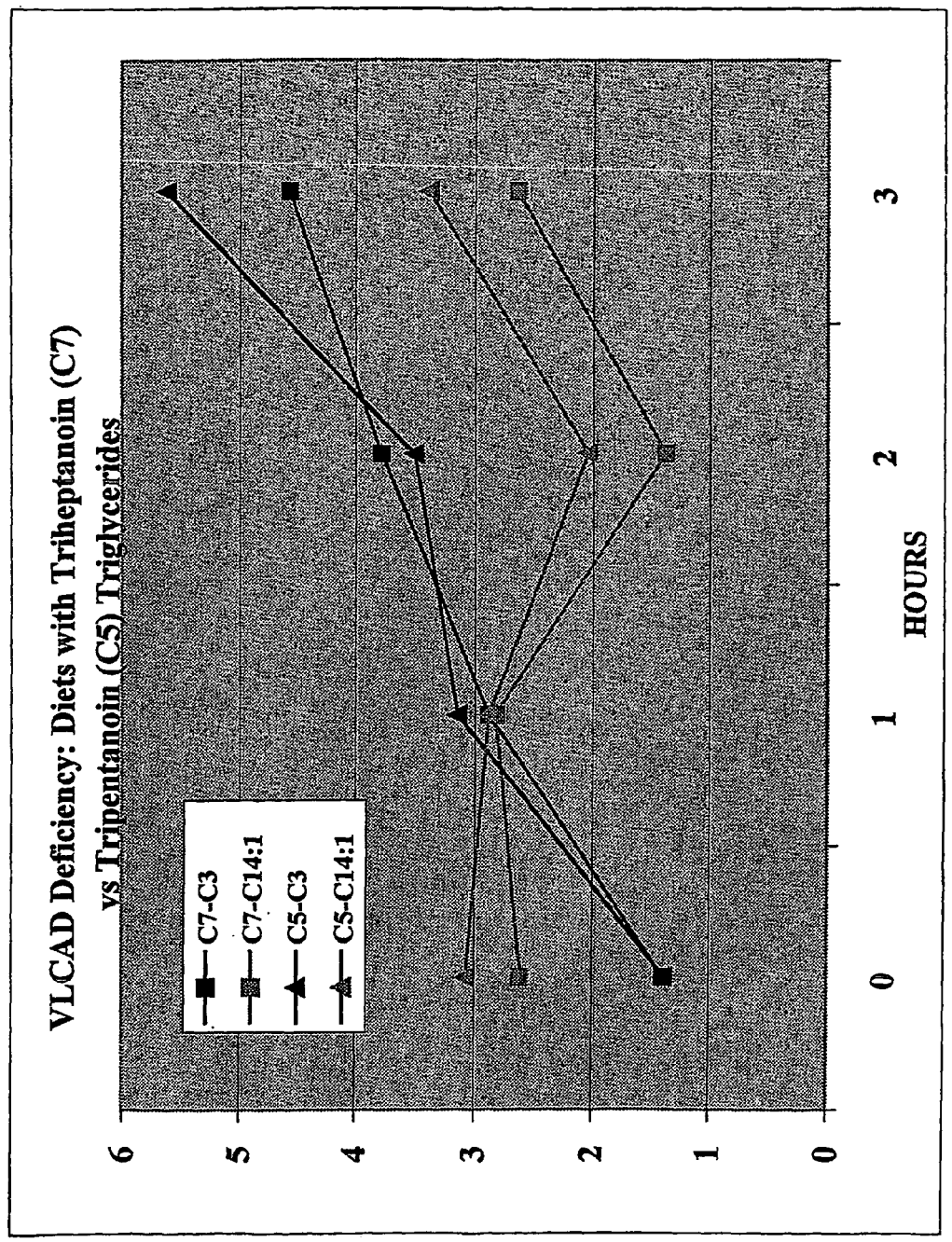
FIG. 3 depicts levels of propionlycarnitine and myristenoylcarnitine in a VCLAD patient on a diet of triheptanoin (C7) or tripentanoin (C5) monitored over a 3 hour interval.

The patient with VLCAD (FIG. 3) was monitored over a 3 hour interval and the SCAD patient was monitored for 4 hours after beginning the meal. There was no clinical or biochemical toxicity associated with these tests. One way the VLCAD patient was monitored was for myristenoylcarnitine (cis-5-C14:1), which reflects oxidation of oleate and is therefore an indication of ongoing lipolysis during the meal tests (it is not derived from either C7 or C5). A reduction of C14:1 associated with increasing levels of C3 (propionylcarnitine) demonstrates complete oxidation for both triglycerides and direct evidence for the inhibition of lipolysis by the anaplerotic effects of these odd-carbon triglycerides. These changes are not observed with even-carbon triglycerides. Results are provided in Table 4 and FIG. 3.

The second patient with SCAD deficiency (FIG. 4) had been receiving the triheptanoin diet for more than 2 years. This disorder is due to an inherited deficiency of butyryl-CoA dehydrogenase (SCAD) and is known to oxidize even carbon fatty acids of 4-6 carbon chain length. The fact that C5 never accumulated during therapy with triheptanoin indicated that C5 was being oxidized by another enzyme in the mitochondrial matrix (presumably isovaleryl-CoA dehydrogenase in the Leucine metabolic pathway). In this patient, there was no limitation in oxidation for either C7 or C5 in the meals. Data is given in Table 5 and shown in FIG. 4.

TABLE 4

VLCAD PATIENT RESULTS

| Time (hours) | Propionylcarnitine Level | | Myristenoylcarnitine Level | |
|---|---|---|---|---|
| | C7 | C5 | C7 | C5 |
| 0 | 1.39 | 1.38 | 2.61 | 3.07 |
| 1 | 2.89 | 3.15 | 2.83 | 2.89 |
| 2 | 3.78 | 3.51 | 1.38 | 2.04 |
| 3 | 4.57 | 5.63 | 2.64 | 3.39 |

TABLE 5

SCAD PATIENT RESULTS

| Time (hours) | Relative Blood Levels of Fatty Acid Chain Lengths After C7 Treatment | | | Relative Blood Levels of Fatty Acid Chain Lengths After C5 Treatment | | |
|---|---|---|---|---|---|---|
| | C3 | C5 | C4 | C3 | C5 | C4 |
| 0 | 3.00 | 0.13 | 0.34 | 2.61 | 0.14 | 0.30 |
| 1 | 2.08 | 0.23 | 0.16 | 2.78 | 0.24 | 0.26 |
| 2 | 2.42 | 0.32 | 0.23 | 3.19 | 0.51 | 0.27 |
| 3 | 3.29 | 0.27 | 0.26 | 3.73 | 0.67 | 0.30 |
| 4 | 2.61 | 0.14 | 0.30 | 4.99 | 0.34 | 0.27 |

Figure 4:
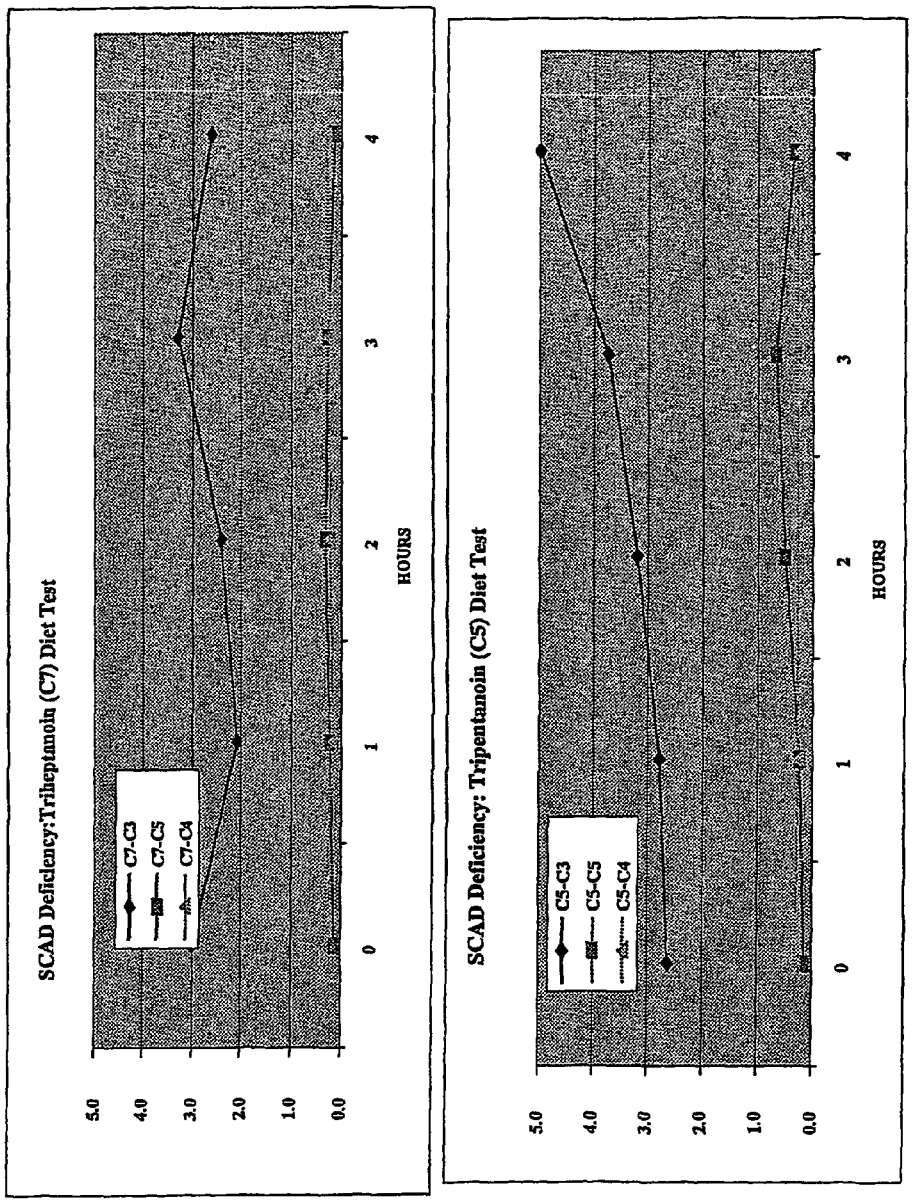
FIG. 4 depicts relative blood levels of fatty acid chain lengths in a SCAD patient following C5 or C7 treatment.

In FIG. 4, C7-C3 represents the blood levels of C3 derived from C7; and C5-C3 represents the blood levels of C3 derived from C5, C7-C5 represents blood levels of pentanoylcarnitine (C5) derived from C7 meals and C5-C5 represents blood levels of pentanoylcarnitine (C5) derived from C5 meals. Neither of these showed any significant on during the course of the meals. C7-C4 and C5-C4 represent the levels of the disease-specific acylcarnitine (butyrylcarnitine [C4]) observed in SCAD deficiency. There was no significant decrease in C4 which was already at very low levels. However, the amount of C3 produced following the meal containing C5 was significantly greater than that observed following ingestion of C7. This increased quantity of C3 corresponds to those observed for SCAD deficiency in the fibroblast studies above shown in Table 1.

EXAMPLE 2

Use of C5 Fatty Acid to Treat Patients with MCAD Deficiency

An infant afflicted with MCAD deficiency would be diagnosed via known screening methods. An infant formula having C5 as the fatty acid source could be fed to the infant, preferably in a manner other than orally due to the disagreeable taste, such as through a feeding tube, to provide a nutrient which will be metabolized into propionyl CoA and acetyl CoA. Oral administration could be employed if a suitable taste-masking agent is available and is employed. Alternatively, the infant could be fed parenterally, such as during periods of illness, with an appropriate parenteral nutrition formula supplemented with C5 fatty acid.

EXAMPLE 3

Use of C15 Fatty Acid in a Nutritional Supplement

A milkshake or smoothie could be formulated with C15 as a fatty acid source or supplement. A person could drink the smoothie and obtain the benefit of a substance that will be metabolized into acetyl CoA as well as propionyl CoA, thus providing fuel for the Krebs cycle from more than one entry point. This could enhance performance of an athlete.

EXAMPLE 4

Use of C5 Fatty Acid in Cardiac Care

A patient that has undergone heart surgery could be supplied C5 fatty acid source via parenteral nutrition. The heart tissue would directly benefit from this energy source, thereby leading to more rapid recovery.

I claim:

1. A method of treating a patient having an fatty acid disorder comprising
identifying a patient having a fatty acid disorder selected from Very-long chain Chain Acyl-CoA Dehydrogenase deficiency (VLCAD), Medium Chain Acyl-CoA Dehydrogenase (MCAD), Short-chain acyl-CoA dehydrogenase (SCAD), mitochondrial trifunctional protein (MTP), and Long-chain 3-hydroxy acyl-coenzyme A dehydrogenase deficiency (LCHAD);
administering to the patient a composition comprising an effective amount sufficient to ameliorate symptoms associated with the fatty acid disorder wherein the composition comprises pentanoin, tripentanoin, pentanoylcarnitine, and n-pentadecanoic acid.

2. The method of claim 1, wherein the fatty acid disorder is a Medium Chain Acyl-CoA Dehydrogenase (MCAD).

3. The method of claim 1, wherein the fatty acid disorder is a Short-chain acyl-CoA dehydrogenase (SCAD).

4. The method of claim 1, wherein the fatty acid disorder is selected from Very-long chain Chain Acyl-CoA Dehydrogenase deficiency (VLCAD), mitochondrial trifunctional protein (MTP), and Long-chain 3-hydroxy acyl-coenzyme A dehydrogenase deficiency (LCHAD).

5. The method of claim 1, wherein the five carbon fatty acid is administered orally.

6. A method for providing rapid nutritional supplementation to a mammalian cell, comprising providing a five carbon fatty acid source selected from pentanoin, tripentanoin, pentanoylcarnitine to the cell.

7. A method for providing nutritional supplementation to a human or animal, comprising providing enterally or parenterally a fatty acid source comprising a five carbon fatty acid source selected from pentanoin, tripentanoin, and pentanoylcarnitine.

8. The method of claim 7, wherein the administration is oral.

9. The method of claim 7, wherein the acquired metabolic derangement concerns increased metabolic needs by cardiac tissue.

10. The dietary formulation of claim 7, wherein the formulation is adapted for consumption by a human during a 24 hour time period and comprises from about 15 to about 40% of the dietary caloric requirement of the human for the 24 hour time period.

11. The method of claim 1, wherein the fatty acid disorder is a Medium Chain Acyl-CoA Dehydrogenase (MCAD).

12. A method of treating a patient having a Medium Chain Acyl-CoA Dehydrogenase (MCAD) fatty acid disorder comprising administering to the patient a composition comprising an effective amount of a five carbon fatty acid source sufficient to ameliorate symptoms associated with the fatty acid disorder selected from pentanoin, tripentanoin, pentanoylcarnitine, and n-pentadecanoic acid.

* * * * *

UNITED STATES PATENT AND TRADEMARK OFFICE
CERTIFICATE OF CORRECTION

PATENT NO. : 8,399,515 B2
APPLICATION NO. : 10/557310
DATED : March 19, 2013
INVENTOR(S) : Charles R. Roe Page 1 of 1

It is certified that error appears in the above-identified patent and that said Letters Patent is hereby corrected as shown below:

In the Claims:

Column 8, Line 67, change "and" to --or--

Signed and Sealed this
Twenty-fifth Day of June, 2013

Teresa Stanek Rea
*Acting Director of the United States Patent and Trademark Office*

UNITED STATES PATENT AND TRADEMARK OFFICE
CERTIFICATE OF CORRECTION

PATENT NO.        : 8,399,515 B2                                              Page 1 of 1
APPLICATION NO.   : 10/557310
DATED             : March 19, 2013
INVENTOR(S)       : Charles R. Roe It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 214 days.

Signed and Sealed this
First Day of September, 2015

Michelle K. Lee
*Director of the United States Patent and Trademark Office*